United States Patent [19]

Tartaglia

[11] Patent Number: 4,484,915
[45] Date of Patent: Nov. 27, 1984

[54] MEDICAL SYRINGE

[76] Inventor: John A. Tartaglia, 108 Stoddard Rd., Waterbury, Conn. 06708

[21] Appl. No.: 479,720

[22] Filed: Mar. 28, 1983

[51] Int. Cl.$^3$ .............................................. A61M 5/00
[52] U.S. Cl. .................................................. 604/227
[58] Field of Search ................ 604/227, 218, 187, 220

[56] References Cited

U.S. PATENT DOCUMENTS

| | | | |
|---|---|---|---|
| 3,316,909 | 5/1967 | Cowley | 604/227 |
| 3,487,834 | 1/1970 | Smith, Jr. et al. | 604/227 |
| 3,990,446 | 11/1976 | Taylor | 604/227 |
| 4,263,911 | 4/1981 | McCormack et al. | 604/227 |

Primary Examiner—John D. Yasko

[57] ABSTRACT

A medical syringe adapted for one hand operation in both aspiration and injection modes, employs an elongated hollow cylinder having at one end a first external flange extending at right angles to the axis of the cylinder and an opening for receiving a piston, the opposite end of the cylinder being adapted to detachably receive a hypodermic needle.

The syringe also employed a piston extending slidably through said opening and being aligned with and centered on the axis of the cylinder, there being a liquid tight seal between said piston and said cylinder, one end of said piston being disposed outside said cylinder, said one end being enlarged and designated as a head, whereby when said cylinder and piston are held in one hand and said first flange and head are squeezed together, injection action ensues.

The syringe also employs a device slidable back and forth along the outer surface of the cylinder, said device including a second flange extending at right angles to said axis and second flange extension elements extending from the second flange slidably over said first flange and engaging said head whereby when said cylinder and piston are held in one hand and said flanges are squeezed together, aspiration action ensues.

4 Claims, 6 Drawing Figures

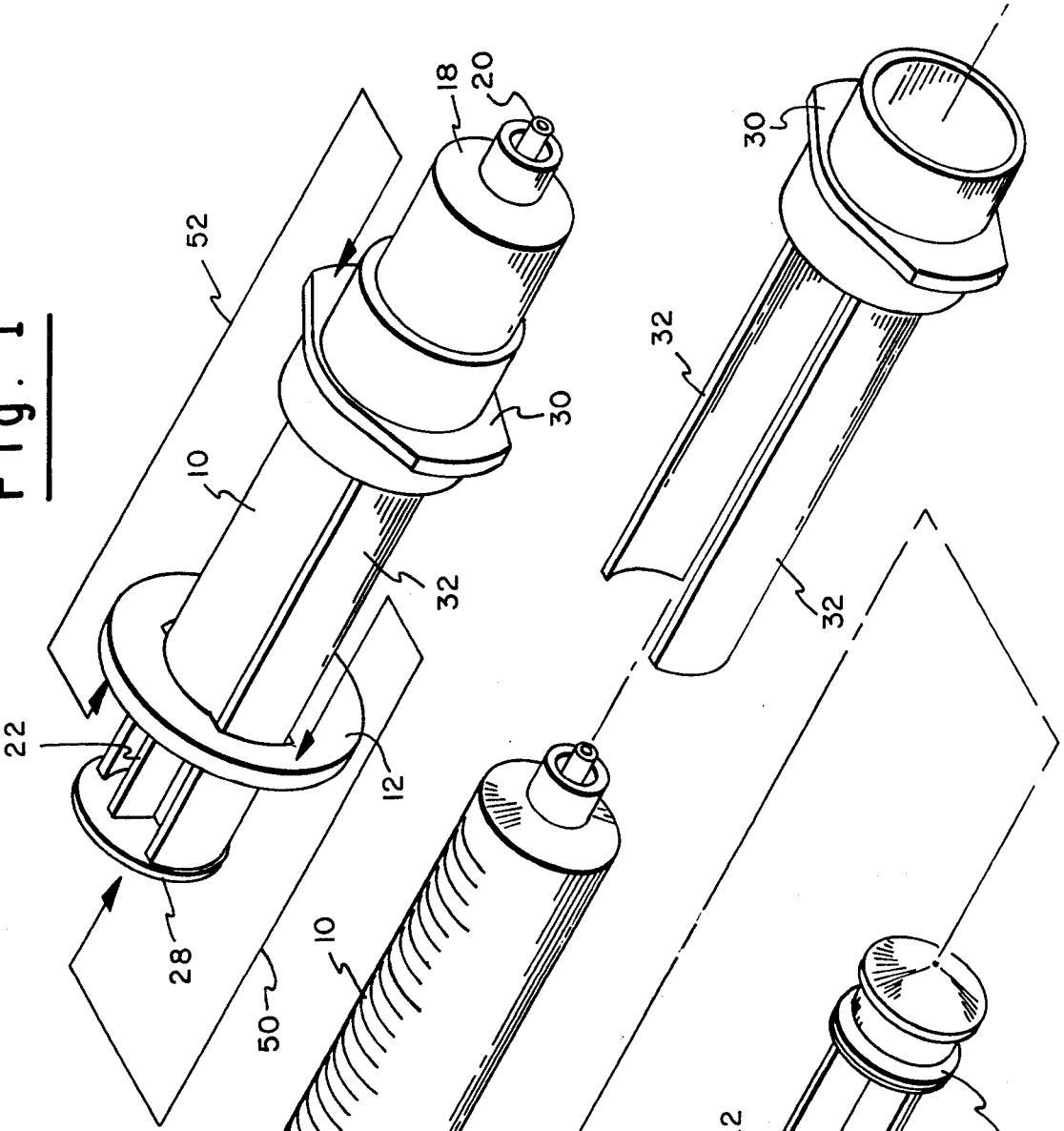
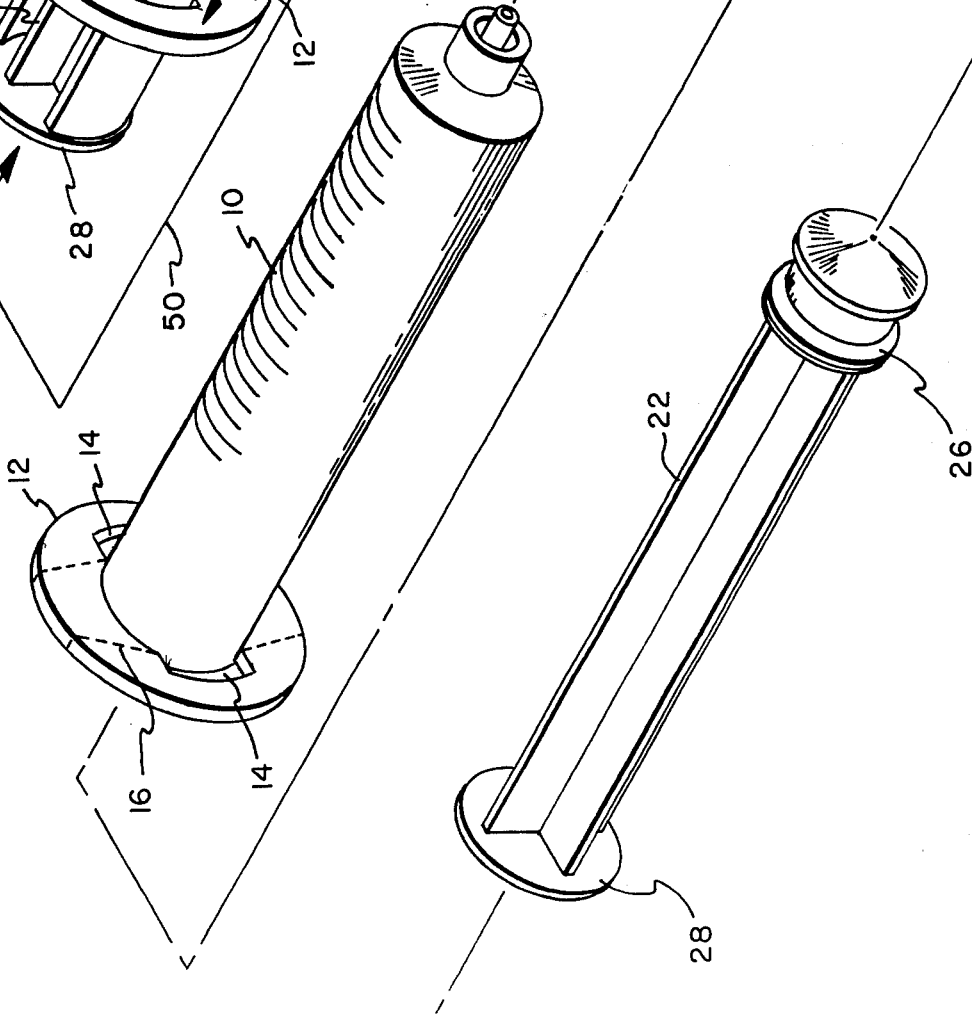

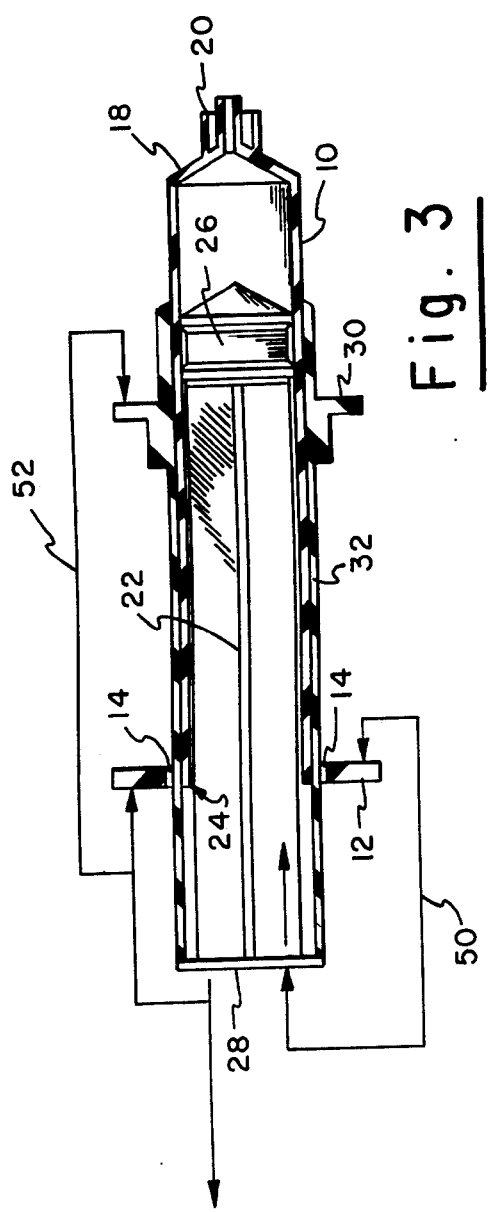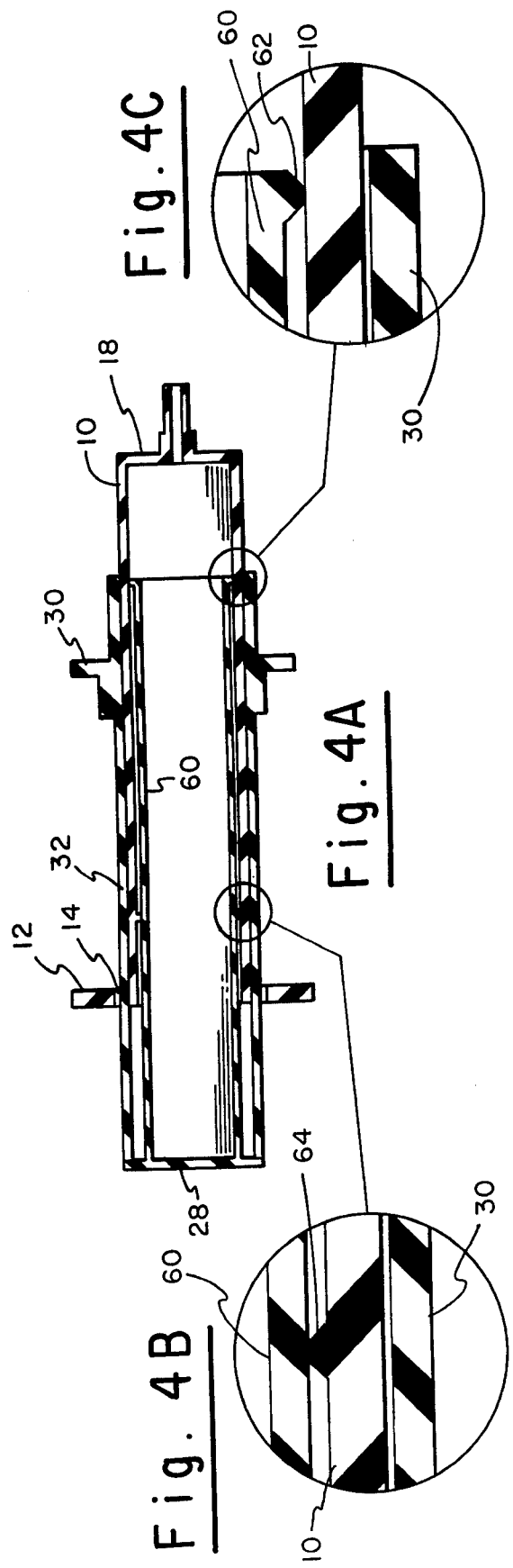

MEDICAL SYRINGE

BACKGROUND OF THE INVENTION

Medical syringes are used in both injection and aspiration modes. Conventionally, when a syringe is used to inject medicine via a needle into a vein or the like, the operator holds the syringe in one hand and squeezes the plunger into the syringe cylinder using the thumb and fingers of the same hand. However, when a syringe is used to aspirate or withdraw blood or other fluid from a needle inserted in a vein or the like, the operator must use two hands, typically holding the cylinder in one hand while pulling the plunger out of the cylinder with the other hand. The present invention overcomes these difficulties by providing a medical syringe which can be held and operated in one hand for both injection and aspiration.

SUMMARY OF THE INVENTION

A medical syringe adapted for one hand operation in both aspiration and injection modes, in accordance with the present invention employs an elongated hollow cylinder having at one end a first external flange extending at right angles to the axis of the cylinder and an opening for receiving a piston, the opposite end of the cylinder having means adapted to detachably receive a hypodermic needle.

The syringe also employs a piston extending slidably through said opening and being aligned with and centered on the axis of the cylinder, there being a liquid tight seal between said piston and said cylinder, one end of said piston being disposed outside said cylinder, said one end being enlarged and designated as a head, whereby when said cylinder and piston are held in one hand and said first flange and head are squeezed together, injection action ensues.

The syringe also employs a device slidable back and forth along the outer surface of the cylinder, said device including a second flange extending at right angles to said axis and second flange extension means extending from the second flange slidably over said first flange and engaging said head whereby when said cylinder and piston are held in one hand and said flanges are squeezed together, aspiration action ensues.

This device can also be detachably secured to known types of syringes whereby these syringes also can be adapted for one hand operation in the asiration mode.

BRIEF DESCRIPTION OF THE DRAWINGS

FIG. 1 is a perspective view of one embodiment of the invention ready for use.

FIG. 2 is an exploded perspective view of the embodiment of FIG. 1.

FIG. 3 is a view in longitudinal cross section of the structure of FIG. 1.

FIG. 4A is a view in longitudinal cross section of a second embodiment of the invention.

FIG. 4B is an enlarged detail view in cross section of a portion of the structure of FIG. 4A as identified by a small circle in FIG. 4A connected by a line to FIG. 4B.

FIG. 4C is another enlarged detail view in cross section of another portion of the structure of FIG. 4A as identified by another small circle in FIG. 4A connected by a line to FIG. 4C.

DETAILED DESCRIPTION OF PREFERRED EMBODIMENTS

Referring first to FIGS. 1-3, an elongated hollow cylinder 10 has at the open end a first flange 12 extending at right angles to the axis of the cylinder. The flange can be circular with two opposite slots 14 or as shown in dotted line at 16 can be elongated and extend in the direction shown. The opposite end of the cylinder as shown 18 can have means 20 adapted to detachably receive a hypodermic needle.

A plunger 22 extends slidably into opening 24 of the open end of the cylinder. The plunger is aligned with and centered on the axis of the cylinder. The plunger has on the end which is disposed within the cylinder a seal 26 whereby a liquid tight seal exists between the piston and the cylinder. One end of the plunger is enlarged and is always disposed outside the cylinder. This end designated as a head is shown at 28.

When the first flange 12 and the head 28 are squeezed together, as indicated in FIG. 3 by interconnected arrow headed lines 50, injection action ensues.

A second flange 30 extends at right angles to the cylinder and has an opening through which the cylinder extends whereby the second flange is slidable back and forth along the outer surface of the cylinder in the axial direction. Two oppositely disposed axially extending members or elements 32 are each secured at one end to flange 30 and extend along the surface of the cylinder through slots 14 (if flange 12 is circular) or along the narrow sides of the flange 12 (if this flange is elongated) toward head 28.

When the second flange 30 and first flange 12 are squeezed together, as indicated in FIG. 3 by interconnected arrow headed lines 52, aspiration action ensues.

The structure shown in FIGS. 4A, 4B and 4C functions in the same manner as the structure in FIGS. 1-3 but is modified by substituting a plunger 60 which itself is a hollow cylinder for the plunger 22 of FIGS. 1-3.

Plunger 60 has an outwardly extending lip 62 at its inner end which is forced into cylinder 10 over an enlarged inner lip 64 in the cylinder whereby the lip 62 forms the requisite seal. After aspiration the plunger contains the aspirated fluid. The syring can then be held vertically with the plunger disposed below the cylinder. The plunger can then be pulled out of the cylinder and used as a vessel, capped if necessary to transport the fluid for testing or other purposes.

What is claimed is:

1. A medical syringe adapted for one hand operation in both aspiration and injection modes, said syringe comprising:

an elongated hollow cylinder having at one end a first external flange having cut out regions and extending at right angles to the axis of the cylinder and an opening for receiving a piston, the opposite end of the cylinder having means adapted to detachably receive a hypodermic needle:

a piston somewhat longer than the cylinder which extends slidably through said opening and is aligned with and centered on the axis of the cylinder, there being a liquid tight seal between said piston and said cylinder, one end of said piston being disposed outside said cylinder, said one end being enlarged and designated as a head, whereby when said cylinder and piston are held in one hand and said first flange and head are squeezed together, injection action ensues; and a device slidable back and forth along the outer surface of the cylinder, said device including a second flange extending at right angles to said axis and second flange extension members extending from the second flange slidably through the regions of said first flange and engaging said head whereby when said cylinder and piston are held in one hand and said flanges are squeezed together, aspiration action ensues.

2. The syringe of claim 1 wherein said members are oppositely disposed parallel and axially elongated, said members being secured at one set of corresponding ends to the second flange, the other set of corresponding ends of said members bearing against said head.

3. The syringe of claim 2 wherein said regions are slots.

4. The syringe of claim 3 wherein said piston is a hollow cylinder sealed at its head and open at its opposite end.

* * * * *